(12) United States Patent
Chang (10) Patent No.: US 6,553,253 B1
(45) Date of Patent: Apr. 22, 2003

(54) METHOD AND SYSTEM FOR ELECTROKINETIC DELIVERY OF A SUBSTANCE

(75) Inventor: Kuo-Wei Chang, Waltham, MA (US)

(73) Assignee: Biophoretic Therapeutic Systems, LLC, Framingham, MA (US)

( * ) Notice: Subject to any disclaimer, the term of this patent is extended or adjusted under 35 U.S.C. 154(b) by 0 days.

(21) Appl. No.: 09/523,217

(22) Filed: Mar. 10, 2000

Related U.S. Application Data (60) Provisional application No. 60/123,934, filed on Mar. 12, 1999.

(51) Int. Cl.[7] .................................................. A61N 1/30
(52) U.S. Cl. .................... 604/20; 607/148; 604/501
(58) Field of Search .......................... 604/20, 501, 19; 128/172.1, 207.21, 172; 607/148

(56) References Cited

U.S. PATENT DOCUMENTS

| | | |
|---|---|---|
| 279,524 A | 6/1883 | Beaty |
| 3,163,166 A | 12/1964 | Brant et al. |
| 3,298,368 A | 1/1967 | Charos |
| 4,116,238 A | 9/1978 | Pettijohn .................. 128/172.1 |
| 4,292,968 A | 10/1981 | Ellis ........................ 128/207.21 |
| 4,383,529 A | 5/1983 | Webster |
| 4,406,658 A | 9/1983 | Lattin et al. .................... 604/20 |
| 4,474,570 A | 10/1984 | Ariura et al. |
| 4,510,939 A | 4/1985 | Brenman et al. |
| 4,689,039 A | 8/1987 | Masaki |
| 4,702,732 A | 10/1987 | Powers et al. |
| 4,747,819 A | 5/1988 | Phipps et al. |
| 4,787,888 A | 11/1988 | Fox |
| 4,838,273 A | 6/1989 | Cartmell |
| 4,919,648 A | 4/1990 | Sibalis |
| 4,953,565 A | 9/1990 | Tachibana et al. |
| 4,979,938 A | 12/1990 | Stephen et al. |
| 4,997,418 A | 3/1991 | DeMartini |
| 5,019,034 A | * 5/1991 | Weaver et al. ................. 604/20 |
| 5,042,975 A | * 8/1991 | Chien et al. ................... 604/20 |
| 5,135,478 A | * 8/1992 | Sibalis ......................... 604/20 |
| 5,160,316 A | 11/1992 | Henley |

(List continued on next page.)

FOREIGN PATENT DOCUMENTS

| | | | |
|---|---|---|---|
| AT | 0232642 | 3/1964 | ................... 604/20 |
| FR | 1445703 | 6/1966 | ................... 604/20 |
| GB | 0299553 | 11/1928 | ................... 604/20 |

OTHER PUBLICATIONS

"Iontophoretic Treatment of Oral Herpes," Henley et al.; Laryngoscope, vol. 94, No. 1, pp. 118–121, Jan. 1984.

"Iontophoretic Application of Idoxuridine for Recurrent Herpes Labialis: Report of Preliminary Chemical Trials," Gangarosa et al.; Meth. And Find. Exptl. Clin. Pharmacol. 1(2), pp. 105–109 (1979).

(List continued on next page.)

Primary Examiner—Ira S. Lazarus
Assistant Examiner—Tu Cam Nguyen

(57) ABSTRACT

An electrokinetic system for delivering a substance into tissue includes an alternating current source of a predetermined frequency. A first electrode is coupled to a first terminal of the alternating current source and a second electrode is coupled to a second terminal of the alternating current source. A rectifying circuit is coupled between the first electrode and the first terminal of the alternating current source. One of the first and second electrodes is adapted for electrical contact with a substance-delivery site. A current rectified by the rectifying circuit flows in a current path between the first and second electrodes when the one of the first and second electrodes is in electrical contact with the substance-delivery site to effect delivery of the substance into the tissue.

53 Claims, 4 Drawing Sheets

U.S. PATENT DOCUMENTS

| | | |
|---|---|---|
| 5,162,042 A | 11/1992 | Gyory et al. |
| 5,203,768 A | 4/1993 | Haak et al. |
| 5,250,022 A | 10/1993 | Chien et al. |
| 5,279,543 A | 1/1994 | Glikfeld et al. |
| 5,298,017 A | 3/1994 | Theeuwes et al. |
| 5,312,326 A | 5/1994 | Myers et al. |
| 5,314,502 A | 5/1994 | McNichols et al. |
| 5,331,979 A | 7/1994 | Henley |
| 5,362,307 A | 11/1994 | Guy et al. |
| 5,362,308 A | 11/1994 | Chien et al. |
| 5,395,310 A | 3/1995 | Untereker et al. |
| 5,415,629 A | 5/1995 | Henley |
| 5,421,816 A | 6/1995 | Lipkovker |
| 5,441,936 A | 8/1995 | Houghten et al. |
| 5,458,569 A | 10/1995 | Kirk et al. |
| 5,464,387 A | 11/1995 | Haak et al. |
| 5,466,217 A | 11/1995 | Myers et al. |
| 5,470,349 A | 11/1995 | Kleditsch et al. |
| 5,540,669 A * | 7/1996 | Sage, Jr. et al. ............... 604/20 |
| 5,551,953 A * | 9/1996 | Lattin et al. ................... 604/20 |
| 5,558,632 A | 9/1996 | Lloyd et al. |
| 5,562,607 A | 10/1996 | Gyory |
| 5,589,563 A | 12/1996 | Ward et al. |
| 5,607,691 A | 3/1997 | Hale et al. |
| 5,618,275 A | 4/1997 | Bock |
| 5,658,247 A | 8/1997 | Henley |
| 5,667,487 A | 9/1997 | Henley |
| 5,676,648 A * | 10/1997 | Henley ......................... 604/20 |
| 5,697,896 A | 12/1997 | McNichols et al. |
| 5,700,457 A | 12/1997 | Dixon |
| 5,711,761 A | 1/1998 | Untereker et al. |
| 5,713,846 A | 2/1998 | Bernhard et al. |
| 5,722,397 A | 3/1998 | Eppstein |
| 5,725,817 A | 3/1998 | Milder |
| 5,788,666 A | 8/1998 | Atanasoska |
| 5,795,321 A | 8/1998 | McCarthur et al. |
| 5,797,867 A | 8/1998 | Guerrera et al. |
| 5,830,175 A | 11/1998 | Flower |
| 5,840,057 A | 11/1998 | Aloisi |
| 5,865,786 A * | 2/1999 | Sibalis et al. .................. 604/20 |
| 5,879,323 A | 3/1999 | Henley |
| 5,899,876 A * | 5/1999 | Flower ......................... 604/20 |
| 5,908,401 A | 6/1999 | Henley |
| 5,919,155 A | 7/1999 | Lattin et al. |
| 5,954,684 A * | 9/1999 | Flower et al. ................. 604/20 |
| 5,961,482 A * | 10/1999 | Chien et al. ................... 604/20 |
| 6,148,232 A * | 11/2000 | Avrahami ..................... 604/20 |

OTHER PUBLICATIONS

"Iontophoresis of Vidarabine Monophosphate for Herpes Orolabialis," Gangarosa et al.; The Journal of Infectious Diseases, vol. 154, No. 6, pp. 930–934, Dec. 1986.

"The Natural History of Recurrent Herpes Simplex Labialis," Spruance et al.; The New England Journal of Medicine, vol. 297, No. 2, pp. 69–75, Jul. 14, 1977.

"Infection with Herpes–Simplex Viruses 1 and 2," Nahmias et al.; The New England Journal of Medicine, pp. 667–674, Sep. 27, 1973.

"Anesthesia of the Human Tympanic Membrane by Iontophoresis of a Local Anesthetic," Comeau et al.; The Laryngoscope, 88:1978, pp. 277–285.

"Iontophoretic Application of Drugs," Waud, J. Appl. Physiol. 23(1), 1967, pp. 128–130.

"Antibiotic Iontophoresis in the Treatment of Ear Chondritis," LaForest et al., Physical Therapy, vol. 58, No. 1, Jan. 1978, pp. 32–34.

"The Quantity and Distribution of Radiolabeled Dexamethasone Delivered to Tissue by Iontophoresis," Glass et al.; International Journal of Dermatology, vol. 19, Nov. 1980, pp. 519–525.

"Iontophoretic Application of Antiviral Chemotherapeutic Agents," Hill et al., Annals New York Academy of Sciences, pp. 604–612.

"Ocular Iontophoresis," Hill et al. Paper, Louisiana State University Medical Center, School of Medicine, New Orleans, Louisiana, pp. 331–354.

"Iontophoretic Application of Adenine Arabinoside Monophosphate to Herpes Simplex Virus Type 1–Infected Hairless Mouse Skin," Park et al.; Antimicrobial Agents and Chemotherapy, vol. 14, No. 4, Oct., 1978, pp. 605–608.

"Iontophoresis: Applications in Transdermal Medication Delivery," Costello et al.; Physical Therapy, vol. 75, No. 6, pp. 104/554–113/563, Jun. 1995.

Physical Enhancement of Dermatologic Drug Delivery: Iontophoresis and Phonophoresis,: Kassan et al.; Journal of the American Academy of Dermatology, Apr. 1996, pp. 657–666.

"Ionotophoresis and Herpes Labialis," Boxhall et al.; The Medical Journal of Australia, May 26, 1984, pp. 686–687.

"A Method of Antibiotic Administration in the Burn Patient," Rapperport et al.; Plastic and Reconstructive Surgery, vol. 36, No. 5, pp. 547–552.

"Iontophoresis for Enhancing Penetration of Dermatologic and Antiviral Drugs," Gangarosa et al., Journal of Dermatology, vol. 22, No. 11, pp. 865–875, Nov. 1995.

"Iontophoretic Treatment of Herpetic Whitlow," Gangarosa et al., Arch. Phys. Med. Rehabil., vol. 70, Apr. 1989.

"Iontophoretic Application of Antiviral Drugs," Gangarosa et al., Proceedings of an International Symposium held in Tokushima City, Japan, pp. 200–204, Jul. 27–30, 1981.

"Iontophoretic Application of Adenine Arabinoside Monophosphate for the Treatment of Herpes Simplex Virus Type 2 Skin Infections in Hairless Mice," Gangarosa, The Journal of Infectious Diseases, vol. 140, No. 6, pp. 1014, Dec. 1979.

"Effect of Iontophoretic and Topical Application of Antiviral Agents in Treatment of Experimental HSV–1 Keratitis in Rabbits," Kwon et al., Investigative Ophthalmology & Visual Science, vol. 18, No. 9, pp. 984–988, Sep., 1979.

"Acyclovir and Vidarabine Monophosphate: Comparison of Iontophoretic and Intravenous Administration for the Treatment of HSV–1 Stromal Keratitis," Hill et al., The American Journal of Medicine, Acyclovir Symposium, pp. 300–304.

"Thymine Arabinoside (Ara–T) Topical and Iontophoretic Applications for Herpes Simplex Virus Type 1 and Type 2 Skin Infections in Hairless Mice," Hill et al., Meth. And Find. Exptl. Clin. Pharmacol. 6(1), pp. 17–20, 1984.

"Iontophoresis Enhances the Transport of Acyclovir Through Nude Mouse Skin by Electrorepulsion and Electroosmosis," Volpato et al., Pharmaceutical Research, vol. 12, No. 11, pp. 1623–1627, 1995.

"Early Application of Topical 15% Idoxuridine n Dimethyl Sulfoxide Shortens the Course of Herpes Simplex Labialis: A Multicenter Placebo–Controlled Trial," Spruance et al., The Journal of Infectious Diseases, 1990; vol. 161; pp. 191–197.

"Iotonphoresis for Surface Local Anesthesia," Gangarosa, JADA, vol. 88, pp. 125–128, Jan. 1974.

"Conductivity of Drugs Used for Iontophoresis," Gangarosa et al., Journal of Pharmaceutical Sciences, vol. 67, No. 10, pp. 1439–1443, Oct., 1978.

"A Pilot Study of Iontophoretic Cisplatin Chemotherapy of Basal and Squamous Cell Carcinomas of the Skin," Chang et al., Arch. Dermatol., vol. 129, pp. 425–427, Apr. 1993.

"How Modern Iontophoresis Can Improve Your Practice," Gangarosa et al.; Oral Surgery, No. 10, Report 2135, Oct. 1982, pp. 1027–1038.

"Postherpetic Neuralgia," Baron et al.; Brain (1993), 116, pp. 1477–1496.

"Iontophoretic Assistance of 5–Iodo–2'–Deoxyuridine Penetration into Neonatal Mouse Skin and Effects of DNA Synthesis," Gangarosa et al., Society for Experimental Biology and Medicine, pp. 439–443, 1977.

"Electrophoretic Evaluation of the Mobility of Drugs Suitable for Iontophoresis," Kamath et al., Meth. Find., Exp. Clin. Pharmacol., 1995, 17(4): pp. 227–232.

"Passive versus Electrotransport–Facilitated Transdermal Absorption of Ketorolac," Park et al.; Clinical Pharmacology & Therapeutics, vol. 63, No. 3, pp. 303–315.

"Transdermal Drug Delivery by Passive Diffusion and Iontophoresis: A Review," Singh et al.; Medicinal Research Reviews, vol. 13, No. 5, 1993, pp. 570–621.

* cited by examiner

FIG. 2
Source Risk-Current Limits

METHOD AND SYSTEM FOR ELECTROKINETIC DELIVERY OF A SUBSTANCE

CROSS-REFERENCE TO RELATED APPLICATION

This application claims priority from U.S. Application No. 60/123,934, filed Mar. 12, 1999, the contents of which are incorporated herein in their entirety.

BACKGROUND OF THE INVENTION

The present invention generally relates to the electrokinetic delivery of a substance (for example, a medicament) into tissue and, more particularly, to a method and system for such delivery that satisfies certain risk criteria for medical equipment that maintains direct electrical contact with human skin. The majority of applications using the present invention are for applying medicaments to treatment sites and therefore the term medicament is used in lieu of the term substance throughout this description.

One type of electrokinetic delivery mechanism is iontophoresis. Iontophoresis is the transfer of ionic agents into tissue by means of electricity. The active component of the medicament, either directly ionizable or attached to a carrier ion and either positively or negatively charged, is driven into the tissue by a properly biased electrode through barriers such as animal (including human) skin, cell and mucosal membranes and other barrier surfaces. Iontophoresis has been used to deliver, among other things, morphine HCL for postoperative pain relief, topical anesthetics (such as lidocaine) for transdermal anesthetization, anti-viral agents for herpes infection, and anti-fungal medicines for athlete's foot. The use of iontophoretic transdermal or transmucocutaneous delivery techniques obviates the need for hypodermic injection for many medicaments, thereby eliminating the concomitant problems of trauma, pain and risk of infection to the patient. Such delivery techniques may also be utilized for controlled or localized treatment especially when a substantial systemic involvement of the medicament is unwanted or harmful.

Figure 1:
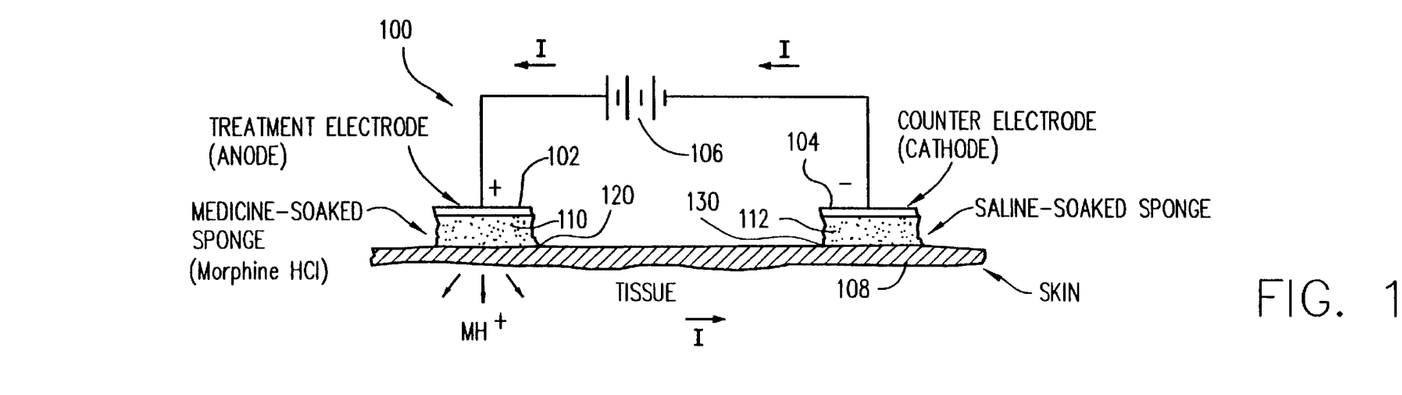
FIG. 1 shows a conventional iontophoretic delivery system 100.

Regardless of the charge of the medicament to be administered, conventional iontophoretic delivery devices typically employ two electrodes (an anode and a cathode). In conjunction with the patient's skin or mucosa, the first (applicator or treatment) electrode is positioned at a treatment site on the skin or mucosa, and the second (counter) electrode is affixed to a second site on the skin or mucosa. These electrodes form a current path that enhances the rate of penetration of the medicament into the treatment site adjacent to the applicator electrode. A conventional iontophoretic delivery system 100 is shown in FIG. 1. System 100 includes a treatment electrode (anode) 102 and a counter electrode (cathode) 104 connected to a DC power supply 106. Electrodes 102 and 104 are in electrical contact with the skin or mucosa via conductive layers 110 and 112, respectively. Such layers may be part of a single medicament-carrying substrate. The medicament-carrying substrate is generally disposable and non-reusable and may be releasably adherable to the patient's treatment site and/or to electrodes 102 and 104. Conductive layers 110 and 112 are shown in FIG. 1 as comprising a medicine-soaked sponge (e.g., a morphine HCL-soaked sponge) and a saline-soaked sponge, respectively. In use, iontophoretic device 100 is turned on (e.g., by a switch, not shown) and a current flows from treatment electrode 102, through conductive layer 110 and skin plus underlying tissue 108, to counter electrode 104, thereby driving medicament through the treatment site into the skin and underlying tissue.

Although use of alternating current has been reported (see, e.g., U.S. Pat. No. 5,224,927), direct current is generally preferred in iontophoresis. As set forth in the '927 patent, at AC frequencies higher than approximately 10 Hz, no substantial effective drug delivery takes place. Medicament and other ions merely move to and fro, lacking any net unidirectional movement. For DC iontophoresis, the amount of current used varies from 0.2 to 1 milliampere, which exceeds the risk-current limit of 10 microamperes for medical equipment that maintains direct electrical contact with the patient. There exists, therefore, a potential hazard associated with ventricular fibrillation and cardiac arrest if the current generated during iontophoresis accidentally passes through the patient's heart. In iontophoresis, the rate of drug delivery increases with current. For this reason, higher current is, in principle, always favored because treatment time is proportionally reduced. However, for current exceeding 0.5 to 1 milliampere, the patient will feel an uncomfortable burning sensation. Even at the 0.5 to 1 milliampere range, when the treatment area is relatively small, the resulting high current density can cause severe pain and actual burning and destruction of the skin tissue.

In any case, to remain effective, existing iontophoresis devices may use treatment currents exceeding the established risk-current limit. In order to reduce the ventricular fibrillation risk, some devices limit the separation distance between the treatment and the counter electrode so that the heart is not directly in the current path and is therefore less likely to be included within the fringe electric fields created by the electrodes. However, because electric current always flows through a path of least resistance, the electrode separation distance needs to be large enough so that current is not short-circuited or concentrated between proximal edges of the electrodes (i.e., between edges 120 and 130 in FIG. 1), so that the current distribution under the treatment electrode is relatively uniform for effective drug delivery, and so that there are no hot-spots or areas of high current density to cause discomfort and pain. Such an approach for cardiac risk avoidance can be further compromised in situations where the patient can touch by fingers or hand the skin area near the electrodes such that the treatment current is diverted and passes through the heart via the arm. Some electrophoresis devices use a large separation distance to achieve a uniform current distribution but place the counter electrode in a less accessible location such as the back or the rear shoulder of the patient.

An effective method for self-administration of a medicament into an individual's skin is disclosed in U.S. Pat. No. 5,676,648 and uses a small cylindrical probe in which the treatment applicator electrode is located at the distal end of a counter electrode consisting of a circumferential tactile metal band which provides electrical connection to the individual's finger and hand. The individual's body completes a long electrical circuit path (through the arm and torso), and thus a uniform current distribution and effective medicament delivery is assured.

SUMMARY OF THE INVENTION

It is desirable to use a system and method for electrokinetic delivery of medicament into tissue that reduces hazards associated with introducing electrical currents into the human or animal body.

In accordance with one aspect of the present invention, an electrokinetic system for delivering a substance into tissue includes an alternating current source of a predetermined frequency. A first electrode is coupled to a first terminal of the alternating current source and a second electrode is coupled to a second terminal of the alternating current source. A rectifying circuit is coupled between the first electrode and the first terminal of the alternating current source. One of the first and second electrodes is adapted for electrical contact with a substance-delivery site. A current rectified by the rectifying circuit flows between the first and second electrodes when the one of the first and second electrodes is in electrical contact with the substance-delivery site to effect delivery of the substance into the tissue.

In accordance with another aspect of the present invention, an electrokinetic method for delivering a substance into tissue includes providing a substance at a treatment site. A rectified current is generated from an alternating current source and the rectified current is caused to flow through the substance to deliver the substance into the tissue.

As an example of an electrokinetic delivery mechanism, iontophoresis carried out as described above satisfies the established risk-current limit requirements and eliminates the hazard of ventricular fibrillation. In addition, unidirectional iontopheresis like that of the DC approach can be obtained.

The accompanying drawings, which are incorporated in and constitute a part of the specification, illustrate various embodiments of the present invention and, together with the general description given above and the detailed description provided below, serve to explain the principles of the invention.

DETAILED DESCRIPTION OF THE INVENTION

The present invention is described in the context of exemplary embodiments. However, the scope of the invention is not limited to the particular examples and embodiments described in this specification. Rather the specification merely reflects certain embodiments and serves to illustrate the principles and characteristics of the present invention. Those skilled in the art will recognize that various modifications and refinements may be made without departing from the spirit and scope of the invention.

A method and system for the safe application of an electrokinetic delivery system, such as iontophoresis, is described with reference to FIGS. 2 through 5. The method and system are based on the use of a high frequency rectified current in conjunction with three electrodes, referred to herein as a treatment electrode, a counter electrode and an auxiliary electrode. For purposes of illustration, transdermal delivery of morphine is used as an example. It will of course be appreciated that the method and system described herein are usable in connection with substances generally including natural or homeopathic products that may be outside the definition of medicaments as well as medicaments (e.g., lidocaine for transdermal anesthetization, anti-viral agents for herpes infections, and anti-fungal medicine for athlete's foot) and in connection with barriers other than skin (e.g., cell membranes, mucosal membranes, etc.). By medicament is meant any chemical or biologic that may be used on or administered to humans or animals as an aid in the diagnosis, treatments or prevention of disease or other abnormal or cosmetic condition or for the relief of pain or to control or improve any physiologic or pathologic condition.

Figure 2:
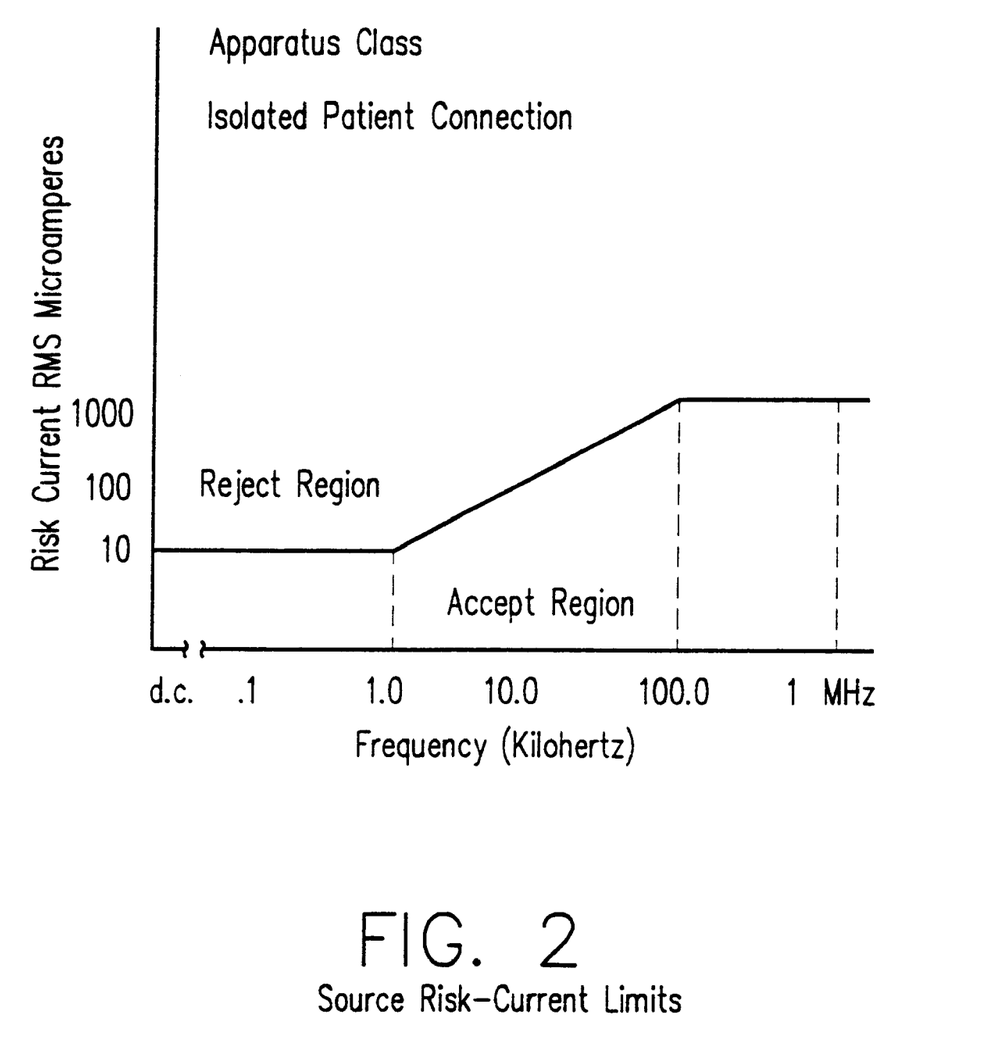
FIG. 2 is a graph of risk current (RMS) in microamperes versus frequency showing the risk current limits based on fibrillatory thresholds.

As described above, iontophoresis involves the use a current to deliver a substance to tissue. In conventional systems, there is a potential hazard associated with ventricular fibrillation and cardiac arrest if the current generated during iontophoresis accidentally passes through the patient's heart. The standard current threshold for ventricular fibrillation risk increases with frequency. FIG. 2 is a graph of risk current (RMS) in microamperes versus frequency showing the risk current limits based on fibrillatory thresholds. For direct current (DC), the limit is 10 microamperes. For frequencies from 1 kilohertz to 100 kilohertz, the risk current limit varies from 10 microamperes to 1 milliampere. For frequencies above 100 kilohertz, but below 1 megahertz, the risk current limit remains at 1 milliampere. See, for example, AAMI (Association for the Advancement of Medical Instrumentation) Standard, "Safe Current Limits Standard."

Figure 3:
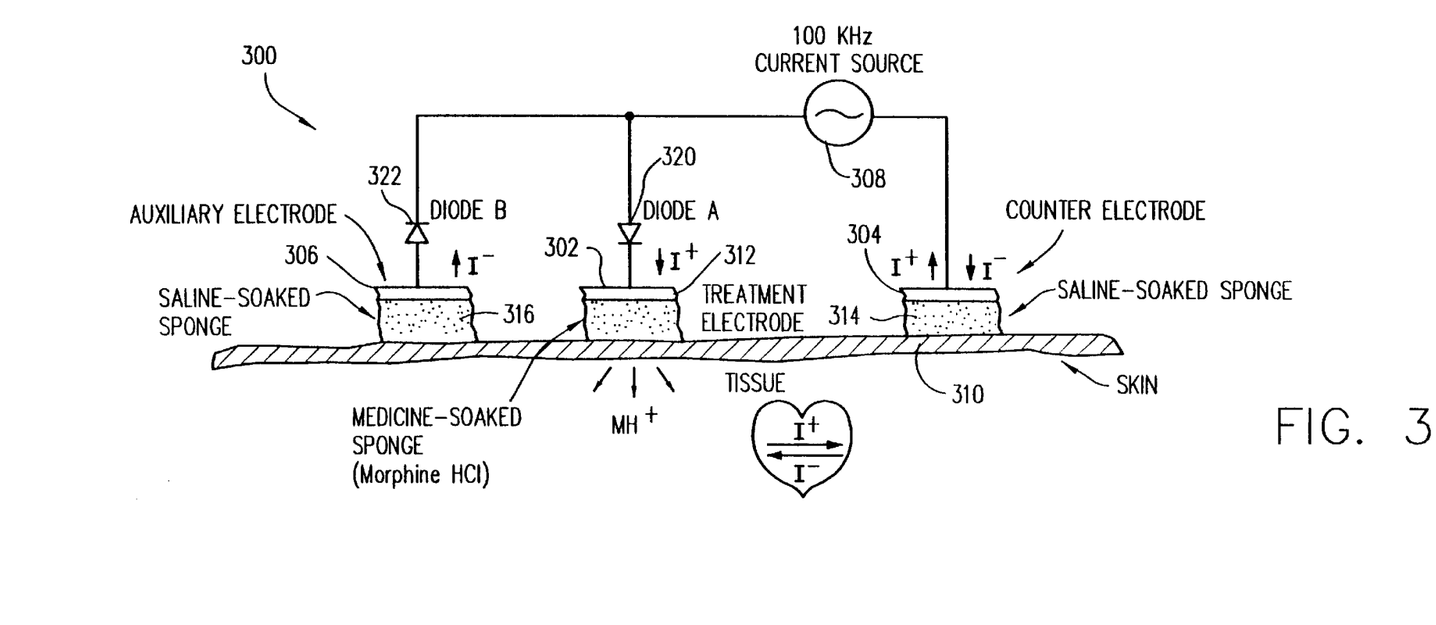
FIG. 3 shows an iontophoretic delivery system 300 in accordance with an embodiment of the present invention.

FIG. 3 shows an iontophoretic delivery system 300 in accordance with an embodiment of the present invention. System 300 includes a treatment electrode 302, a counter electrode 304 and an auxiliary electrode 306 connected to a 100 kilohertz alternating current source 308. Electrodes 302, 304 and 306 are in electrical contact with the patient's skin via conductive layers 312, 314 and 316, respectively. Such layers may, for example, be part of a medicament-carrying substrate or pad. The medicament-carrying substrates or pads are generally disposable and non-reusable and may be releasably adherable to the patient's skin and/or to electrodes 302, 304 and 306. Conductive layer 312 is shown in FIG. 3 as comprising a medicament-soaked sponge or other porous open cellular material, such as cotton, and conductive layers 314 and 316 are shown in FIG. 3 as each comprising a saline-soaked sponge or other such material.

For example, conductive layer 312 may be of a mesh-like construction having vertical cells dimensioned to accommodate a viscous fluid within the confines of the cellular structures. The viscous fluid contained within the plurality of cells includes a medicament that is in a form suitable for transport under the influence of an electric current. Conductive layers 314 and 316 may be mesh-like tactile conductive portions that contain an electrically conductive gel or fluid therewithin. Each of the conductive layers has a lower skin-facing surface and an upper electrode-facing surface. The cells form apertures between the lower skin-facing surface and the upper electrode-facing surface. The device-facing surfaces of the electrodes may further include an adhesive layer applied thereto for suitably releasably adhering the electrodes to the iontophoresis device.

Auxiliary electrode 306 is located lateral to, behind or near treatment electrode 302. Auxiliary electrode 306 and treatment electrode 302 can be in close proximity to each other and the area of auxiliary electrode 306 can be very small compared to the area of treatment electrode 302. These features permit design of a compact hand-held unit in spite of the addition of an auxiliary electrode. In one particular implementation, the total area can be reduced to a minimum by placing auxiliary electrode 306, in the form of a metal mesh, in front of treatment electrode 302. The open mesh allows free passage of medicament and ions to and from treatment electrode 302. Of course, auxiliary electrode 306 may be positioned elsewhere and the present invention is not limited in this respect.

Treatment electrode 302 is connected to AC source 308 via a current path including a first rectifying element 320 for passing current flowing from AC source 308 to skin (and tissue) 310 and blocking current flowing from skin (and tissue) 310 to AC source 308. In the illustrative FIG. 3 embodiment, first rectifying element 320 is a diode having its anode connected to AC source 308 and its cathode connected to treatment electrode 302. Auxiliary electrode 306 is connected to AC source 308 via a current path including a second rectifying element 322 for passing current flowing from skin (and tissue) 310 to AC source 308 and blocking current flowing from AC source 308 to skin (and tissue) 310. In the illustrative FIG. 3 embodiment, second rectifying element 322 is a diode having its anode connected to auxiliary electrode 306 and its cathode connected to AC source 308. Counter electrode 304 is connected to AC source 308 via a bi-directional current path over which current can flow from AC source 308 to skin (and tissue) 310 and from skin (and tissue) 310 to AC source 308.

In use, treatment electrode 302, counter electrode 304, auxiliary electrode 306 are placed in electrical contact with skin 310 via conductive layers 312, 314 and 316, respectively. Conductive layers 312, 314 and 316 may be releasably attached to the electrodes and/or to skin 310 using, for example, a releasable adhesive. Iontophoretic system 300 is then turned on using, for example, a switch (not shown in FIG. 3). During the positive cycle portions of AC source 308, a component current I$^+$ flows from treatment electrode 302 to the patient's skin and tissue and from the patient's skin and tissue to counter electrode 304. In this way, for example, morphine HCL ions (MH+) are delivered to the tissue covered by the patient's skin. During the negative cycle portions of AC source 308, a component current I$^+$ flows from counter electrode 304 to the patient's skin and tissue and from the patient's skin and tissue to auxiliary electrode 306.

Figure 4:
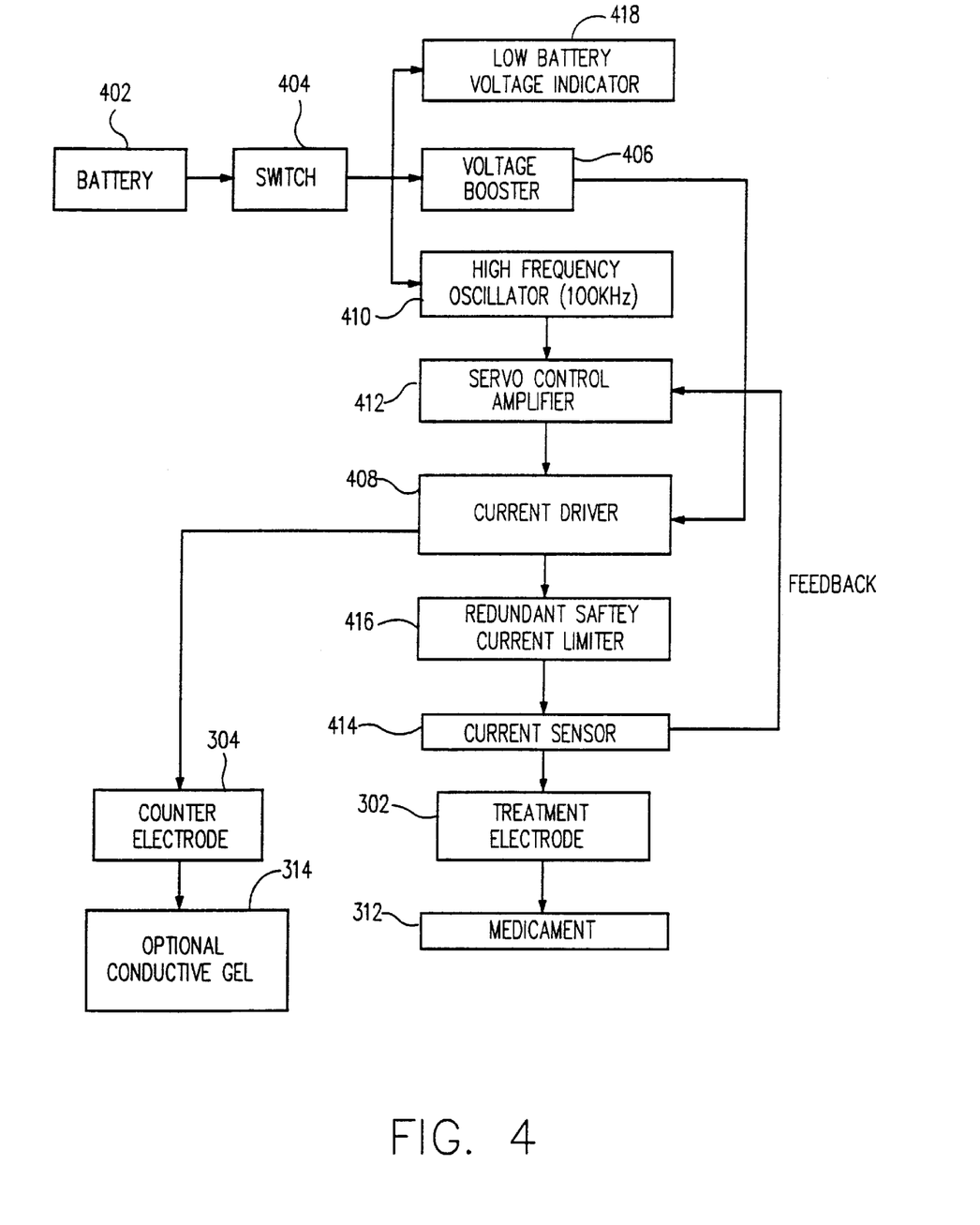
FIG. 4 shows a block diagram of electrical circuit elements of an embodiment of the present invention.

FIG. 4 is a block diagram showing electronic circuit design elements used in an illustrative implementation of a high frequency unidirectional iontophoretic medicator in accordance with an embodiment of the present invention. In this example, power source 402 is a battery comprising one or more AAA-sized primary cells connected either in series or in parallel. Counter electrode 304 is connected to an output of current driver 408 (see FIGS. 4 and 5). An optional conductive layer 314 (such as a conductive gel or a saline-soaked sponge) is used to facilitate current flow to and from the patient's skin. An internal mechanical or electronic switch 404, activated externally by a magnet or magnetic material 520 (see FIG. 5), controls the on and off status of the device. A voltage booster circuit 406 converts the low battery voltage (e.g., 1.5 to 3 VDC) to a high voltage around 30 VDC. The high voltage or high potential is preferred to allow a current driver 408 to overcome any tissue resistance. An oscillator circuit 410 generates a square-wave or sinusoidal AC signal with the selected operating frequency (e.g., 100 kilohertz). A servo-controlled amplifier 412, in synchronization with the oscillator signal, controls the current magnitude based on current feedback signals from a current sensor 414. A current driver stage 408 controls the bias voltage and maintains the desired current to treatment electrode 302. A redundant current limiter 416 is used to provide a safe upper limit for the treatment current. A low battery voltage indicator 418 (e.g., an LED) signals when the battery capacity is low.

Figure 5:
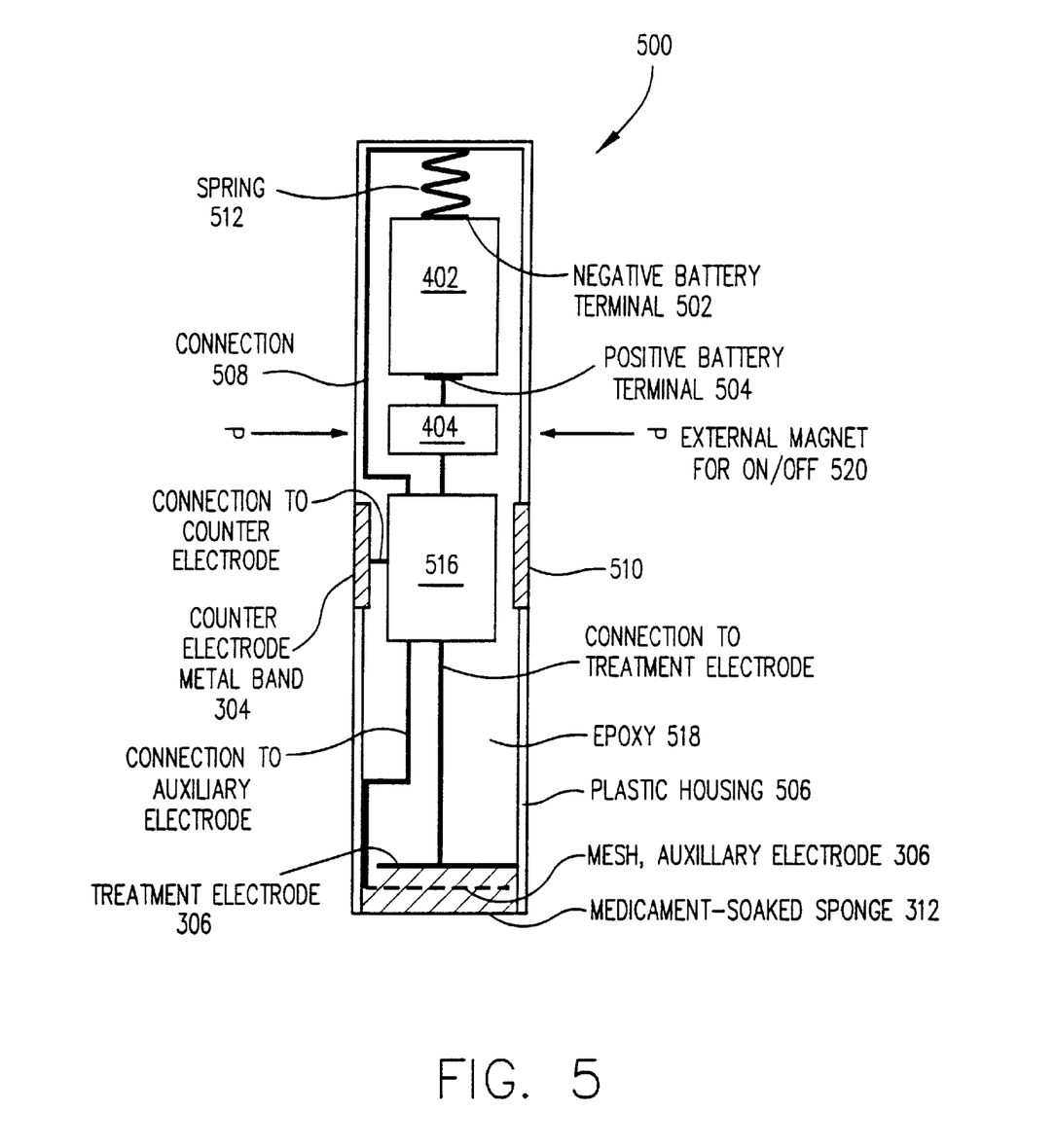
FIG. 5 shows a hand-held device with internal layout of electric and electronic elements.

FIG. 5 illustrates a hand-held device 500 into which the various circuit elements of FIG. 4 may be incorporated. Of course, it will be apparent that the circuit elements of FIG. 4 may be incorporated in a wide variety of devices and the device of FIG. 5 is provided by way of illustration, not limitation. The hand-held device shown in FIG. 5 is configured along the lines of the hand-held devices shown in U.S. Pat. Nos. 5,676,648, 5,879,323 and 5,908,401, the contents of each of which are incorporated herein by reference. For ease of illustration, not all of the elements shown in FIG. 4 are shown in FIG. 5. Housing 506 of the handheld device is preferably formed of plastic and is shaped to comfortably fit within a user's hand. Medicament-soaked sponge 312 is in electrical contact with treatment electrode 306. A mesh or gridded auxiliary electrode 306 is, as an example, interposed between treatment electrode 306 and the patient. Negative battery terminal 502 is connected via an electrical connection 508 to an electronic package 516, and an output of a current drive circuit within electronic package 516 connects to counter electrode 304 provided as a metal band 510 circumferentially (either continuously or discontinuously) formed around housing 506. For the self-administration of medicament, a user touches counter electrode 304 with his/her skin (e.g., fingers). Electrical connection 508 includes a spring portion 512 for holding power source (battery) 402 in place. Positive battery terminal 504 is connected to switch 404 (e.g, a mechanical reed switch or an electronic switch activated by an external magnet denoted at 520). Element 516 in FIG. 5 designates an electronic package at least containing oscillator 410, amplifier 412, current driver 408, redundant safety current limiter 416, current sensor 414 and rectifying elements 320 and 322. Some or all of the components within housing 506 may be contained in epoxy 518.

As described above, in cases in which iontophoresis treatments are administered by a patient without the supervision of medical professionals (e.g., at home), current may accidentally pass through the patient's heart. With conventional equipment, the portion of the current directly traversing the patient's heart could reach a level resulting in ventricular fibrillation. In accordance with the above-described embodiment of the present invention, the frequency of the electrical driving circuit is increased from 0 (DC) to 100 kilohertz. As can be seen with reference to FIG. 2, in this case, the current can be safely increased up to 1 milliampere (RMS). This results in effective delivery of the medicament to the patient. Thus, the use of rectified high-frequency iontophoresis as described above satisfies the established risk-current limit requirements and eliminates the hazard of ventricular fibrillation. In addition, the goal of unidirectional iontophoresis like that of the DC approach can be obtained. Therefore, although the AC current is rectified at the treatment site to obtain DC-like, unidirectional iontophoresis, any current passing through the heart remains strictly bi-directional and alternating with a frequency high enough to meet the risk current requirement.

In rare cases in which AC iontopheresis is applicable, the hazard associated with ventricular fibrillation can also be eliminated by using a high frequency current source around 100 kilohertz. In this special case, rectifying elements and auxiliary electrode 102 are not required because AC iontophoresis is desired. The same circuit design used for unidirectional AC electrophoresis (FIG. 4) is directly applicable.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electrokinetic system for delivering a substance into a body, said system comprising:
   an alternating current source of a predetermined frequency;
   electrodes coupled to said alternating current source, said electrodes including a treatment electrode adapted for electrically contacting a substance-delivery site on the body, a counter electrode and an auxiliary electrode; and
   circuitry coupled between said electrodes and said alternating current source for supplying currents to said electrodes when said electrodes are in electrical contact with the body in order to deliver the substance into the body at the substance-delivery site.

2. The system according to claim 1, wherein the substance-delivery site is animal skin.

3. The system according to claim 2, wherein the animal skin is human skin.

4. The system according to claim 1, wherein the substance-delivery site is a cell membrane.

5. The system according to claim 1, wherein the substance-delivery site is a mucosal membrane.

6. The system according to claim 1, wherein the predetermined frequency of said alternating current source is about 100 kilohertz.

7. The system according to claim 1, wherein the predetermined frequency of said alternating current source is between about 1 kilohertz and 1 megahertz.

8. The system according to claim 1, wherein said treatment electrode electrically contacts the substance-delivery site through an electrode of a substrate carrying the substance.

9. The system according to claim 1, wherein the substance is medicament.

10. The system according to claim 1, wherein said circuitry includes a rectifying circuit for rectifying the current supplied to said treatment electrode.

11. The system according to claim 10, wherein the magnitude of the current rectified by said rectifying circuit is about 1 milliamp (RMS).

12. The system according to claim 10, wherein the magnitude of the current rectified by said rectifying circuit is between about 10 microamps (RMS) and 1 milliamp (RMS).

13. The system according to claim 10, wherein said rectifying circuit is a diode.

14. The system according to claim 1, wherein said circuitry supplies currents to said electrodes so that a uni-directional current flow for delivering the substance into the body is maintained at the substance-delivery site.

15. The system according to claim 1, wherein said circuitry supplies currents to said electrodes so that a uni-directional current flow for delivering the substance into the body is maintained at the substance-delivery site and a bi-directional current flow is maintained through the body.

16. The system according to claim 1, wherein the area of said auxiliary electrode is small compared to the area of said treatment electrode.

17. An electrokinetic system for delivering a substance into a body, said system comprising:
   an alternating current source of a predetermined frequency;
   first and second electrodes coupled to a first terminal of said alternating current source, and a third electrode coupled to a second terminal of said alternating current source; and
   a first rectifying circuit coupled between said first electrode and the first terminal of said alternating current source and a second rectifying circuit coupled between said second electrode and the first terminal of said alternating current source,
   wherein
      said first electrode is adapted for electrical contact with a substance-delivery site on the body, and
      when said electrodes including said first electrode are in electrical contact with said body,
         a current rectified by said first rectifying circuit flows in a current path between said first and third electrodes during first cycle portions of current generated by said alternating current source so as to effect delivery of the substance into the body, and
         a current rectified by said rectifying circuit flows in a current path between said second and third electrodes during second cycle portions of the current generated by said alternating current source.

18. The system according to claim 17, wherein the substance-delivery site is animal skin.

19. The system according to claim 18, wherein the animal skin is human skin.

20. The system according to claim 17, wherein the substance-delivery site is a cell membrane.

21. The system according to claim 17, wherein the substance-delivery site is a mucosal membrane.

22. The system according to claim 17, wherein the predetermined frequency of said alternating current source is about 100 kilohertz.

23. The system according to claim 17, wherein the predetermined frequency of said alternating current source is between about 1 kilohertz and 1 megahertz.

24. The system according to claim 17, wherein the magnitude of the current rectified by said first rectifying circuit is about 1 milliamp (RMS).

25. The system according to claim 17, wherein the magnitude of the current rectified by said first rectifying circuit is between about 10 microamps (RMS) and 1 milliamp (RMS).

26. The system according to claim 17, wherein the first and second rectifying circuits are diodes.

27. The system according to claim 17, wherein an area of said second electrode is less than an area of said first electrode.

28. The system according to claim 17, wherein the substance is medicament.

29. An electrokinetic method for delivering a substance into a body, the method comprising:
   providing a substance at a substance-delivery site on the body;
   placing electrodes coupled to an alternating current source in electrical contact with the body, the electrodes including a treatment electrode adapted for electrical contact with the body at the substance-delivery site; and
   supplying current to said electrodes when said electrodes are in electrical contact with the body so that a uni-directional current flow for delivering the substance into the body is maintained through said treatment electrode at the substance-delivery site and a bi-directional current flow is maintained through the body.

30. The method according to claim 29, wherein the substance-delivery site is animal skin.

31. The method according to claim 30, wherein the animal skin is human skin.

32. The method according to claim 29, wherein the substance-delivery site is a cell membrane.

33. The method according to claim 29, wherein the substance-delivery site is a mucosal membrane.

34. The method according to claim 29, wherein said alternating current source has a frequency of about 100 kilohertz.

35. The method according to claim 29, wherein said alternating current source has a frequency between about 1 kilohertz and 1 megahertz.

36. The method according to claim 29, wherein the magnitude of the uni-directional current is about b 1milliamp (RMS).

37. The method according to claim 29, wherein the magnitude of the uni-directional current is between about 10 microamps (RMS) and 1 milliamp (RMS).

38. The method according to claim 29, wherein the uni-directional current is generated using a diode.

39. The method according to claim 29, wherein the substance is medicament.

40. An electrokinetic drug delivery device for personal use and self-administration of a medicament into an individual's skin, comprising:
an assembly having an outer surface, a portion thereof shaped for grasping within an individual's hand for manual manipulation by the individual;
a self-contained alternating current source of a predetermined frequency within said assembly;
electrodes coupled to said alternating current source, said electrodes including a treatment electrode adapted for electrically contacting a substance-delivery site on the skin, a counter electrode and an auxiliary electrode; and
circuitry coupled between said electrodes and said alternating current source for supplying currents to said electrodes when said electrodes are in electrical contact with the skin in order to deliver the substance into the body at the substance-delivery site.

41. The device according to claim 40, wherein the predetermined frequency of said alternating current source is about 100 kilohertz.

42. The device according to claim 40, wherein the predetermined frequency of said alternating current source is between about 1 kilohertz and 1 megahertz.

43. The device according to claim 40, wherein the magnitude of the unidirectional current is about 1 milliamp (RMS).

44. The device according to claim 40, wherein the magnitude of the unidirectional current is between about 10 microamps (RMS) and 1 milliamp (RMS).

45. The device according to claim 40, wherein the rectifying circuit is a diode.

46. The device according to claim 40, wherein the substance is medicament.

47. The device according to claim 36, wherein said circuitry includes a rectifying circuit for rectifying the current supplied to said treatment electrode.

48. The device according to claim 36, wherein said circuitry supplies currents to said electrodes so that a uni-directional current flow for delivering the substance into the body is maintained at the substance-delivery site.

49. The device according to claim 36, wherein said circuitry supplies currents to said electrodes so that a uni-directional current for delivering the substance into the skin is maintained at the substance-delivery site and a bi-directional current flow is maintained through the skin.

50. The device according to claim 36, wherein the area of said auxiliary electrode is small compared to the area of said treatment electrode.

51. A system for delivering a substance into a body at a treatment site, said system comprising:
an alternating current source;
a plurality of electrodes; and
circuitry connected between the alternating current source and the electrodes for supplying current to said electrodes when said electrodes are in electrical contact with said body so that a uni-directional current flow for delivering the substance into the body is maintained at the treatment site and a bi-directional current flow is maintained through the body.

52. The system according to claim 51, wherein the plurality of electrodes comprises at least three electrodes including a treatment electrode, a counter electrode and an auxiliary electrode.

53. The system according to claim 51, wherein the circuitry comprises one or more rectifiers.

* * * * *